(12) United States Patent  (10) Patent No.: US 8,972,025 B2
Hill et al.  (45) Date of Patent: Mar. 3, 2015

(54) ACTIVE FIXATION IMPLANTABLE MEDICAL LEAD

(75) Inventors: Rolf Hill, Jarfalla (SE); Olof Stegfeldt, Alta (SE)

(73) Assignee: St. Jude Medical AB, Jarfalla (SE)

( * ) Notice: Subject to any disclaimer, the term of this patent is extended or adjusted under 35 U.S.C. 154(b) by 355 days.

(21) Appl. No.: 13/404,771

(22) Filed: Feb. 24, 2012

(65) Prior Publication Data

US 2012/0221085 A1  Aug. 30, 2012

Related U.S. Application Data

(60) Provisional application No. 61/448,381, filed on Mar. 2, 2011.

(30) Foreign Application Priority Data

Feb. 24, 2011  (EP) ..................................... 11155811

(51) Int. Cl.
*A61N 1/00*  (2006.01)
*A61N 1/05*  (2006.01)

(52) U.S. Cl.
CPC ............ *A61N 1/0558* (2013.01); *A61N 1/0563* (2013.01)
USPC ....................................................... 607/116

(58) Field of Classification Search
USPC .......................................... 607/116, 119, 127
See application file for complete search history.

(56) References Cited

U.S. PATENT DOCUMENTS 5,259,395 A * 11/1993 Li ................................. 607/131
2010/0217107 A1 * 8/2010 Hill et al. ...................... 600/377
2010/0234931 A1 * 9/2010 Jarl et al. ...................... 607/149

OTHER PUBLICATIONS

European Search Report, completed Aug. 19, 2011—EP App. No. 11155811.

* cited by examiner

*Primary Examiner* — Christopher D Koharski
*Assistant Examiner* — Nadia A Mahmood (57) ABSTRACT

An implantable medical lead has a distal lead portion with a tubular header and a fixation helix provided in a lumen of the tubular header. The fixation helix is connected to a shaft attached to a conductor coil. A tubular coupling is connected to the tubular header and is coaxially arranged relative the shaft, with the shaft in its lumen. Rotation of the conductor coil causes rotation of the shaft and the fixation helix and longitudinal movement of the fixation helix out of the implantable medical lead by a rotation-to-translation transforming element. A friction device is arranged between the shaft and the tubular coupling or between the tubular header to oppose rotation of the shaft relative the tubular header and the tubular coupling.

16 Claims, 8 Drawing Sheets

ACTIVE FIXATION IMPLANTABLE MEDICAL LEAD

CROSS REFERENCE TO RELATED APPLICATIONS

This application claims priority from European Patent Application No. 11155811.0, filed Feb. 24, 2011, and U.S. Provisional Patent Application Ser. No. 61/448,381, filed Mar. 2, 2011.

FIELD OF THE INVENTION

The present invention generally relates to implantable medical leads, and in particular to implantable medical leads of the active fixation type.

BACKGROUND OF THE INVENTION

Various types of body-implantable medical leads are known and used within the medical field. For example, implantable medical devices (IMDs), such as pacemakers, cardiac defibrillators and cardioverters, are, in operation, connected to implantable medical leads for sensing cardiac function and other diagnostic parameters and delivering stimulation pulses.

Implantable medical leads can broadly be divided into two different groups depending on the fixation and anchoring to tissue in the subject's body. A first group includes implantable medical leads of the so-called passive fixation type. Such an implantable medical lead comprises a physical structure close to the distal end of the implantable medical lead. Following implantation the implantable medical lead and in particular the distal end that is brought into contact with the target tissue in the subject's body will be covered by a fibrin clot and connective tissue. The physical structure is then entangled in the connective tissue and is thereby anchored to the target tissue. Examples of such physical structures employed in the art of implantable medical leads of the passive fixation type include collar, tines and fins.

The second group includes implantable medical leads of the so-called active fixation type. These implantable medical leads comprise a fixation structure that is actively fixed and anchored to the target tissue. The fixation structure is typically in the form of a helix or screw-like element that is actively screwed into the target tissue to thereby anchor the implantable medical lead.

Figure 10A:
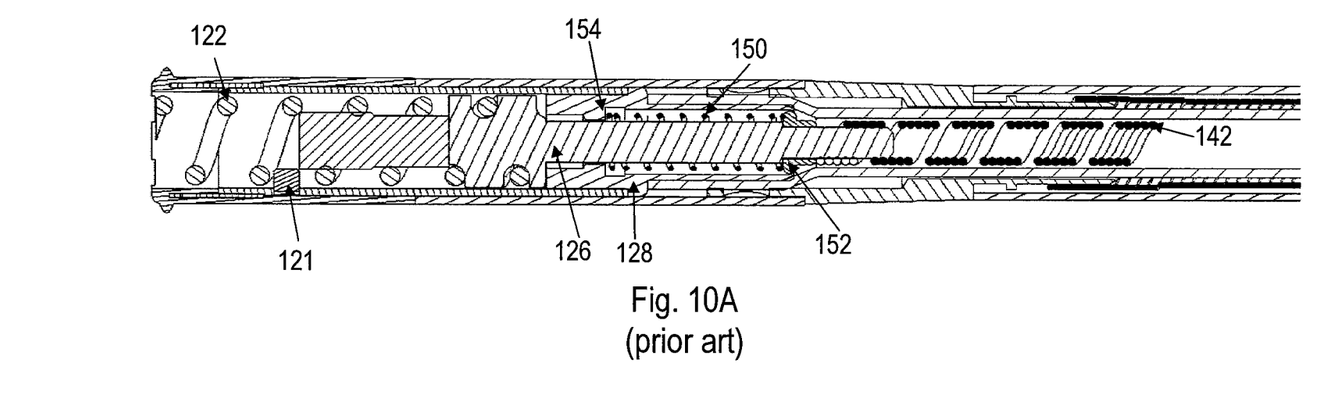
FIGS. 10A and 10B are cross-sectional views of a distal header assembly of an implantable medical lead according to prior art.
Figure 10B:
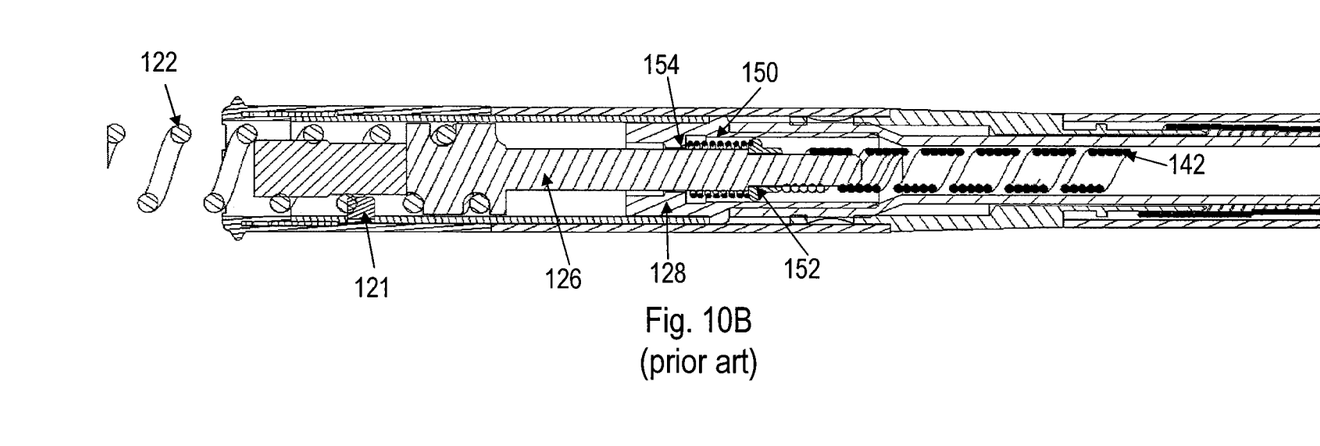

Today implantable medical leads of the active fixation type are most common due to, among others, more reliable tissue fixation. Though generally preferred over the passive fixation type these implantable medical leads may have their shortcomings and disadvantages. FIGS. 10A and 10B are cross-sectional views of an example of the distal portion of a prior art implantable medical lead of the active fixation type. In order to extend the fixation helix 122 into the target tissue a torque is applied to a connector pin at the opposite, proximal portion of the implantable medical lead. The applied torque causes, due to a mechanical connection between the connector pin and a conductor coil 142, rotation of the conductor coil 142 and a shaft 126 mechanically connected to the conductor coil 142. This shaft 126 in turn interconnects the fixation helix 122 to the conductor coil 142 and thereby causes a rotation of the fixation helix 122 when the conductor coil 142 is rotated. Rotation of the fixation helix 122 is translated into a longitudinal movement of the fixation helix 122 out of the distal portion of the implantable medical lead through the action of a post 121 protruding between adjacent turns of the fixation helix 122.

In order to prevent unintentional movement of the fixation helix 122 out of the distal portion, e.g. during implantation of the implantable medical lead through the vascular system of the subject, a contact spring 150 is provided between a shoulder 154 of a fixed coupling 128 and a stop structure 152 attached to the outer or lateral surface of the shaft 126. The contact spring 150 further defines the final helix extension length as illustrated in FIG. 10B, where this final helix extension length is reached when the contact spring 150 is fully compressed between the shoulder 154 and the stop structure 152. A further function of the contact spring 150 is to establish electrical contact between the shaft 126 and the coupling 128 in order to eliminate chatter problems that can occur between the shaft 126 and the coupling 128 due to a free floating potential in the coupling 128 relative the shaft 126, the fixation helix 122 and the conductor coil 142.

However, the contact spring 150 may create an increased friction between the post 121 and the fixation helix 122. This can be experienced as a non-repeatable helix performance since the induced friction can vary from one implantable medical lead to another implantable medical lead. Another issue is the risk of jumpiness during extension and retraction of the fixation helix 122 and the risk of a jammed but not fully extended fixation helix 122. These problems can be caused by the end of the contact spring 150 getting into or at least trying to get into the space between the coupling 128 and the shaft 126. Furthermore, as mentioned above, the final helix extension length is dictated by the compression of the contact spring 150. The compression of the contact spring 150 may, however, vary from contact spring to contact spring due to small variations in wire diameter, number of turns and spring end configurations. Furthermore, in some lead designs, compressed turns of the contact spring 150 could sometimes become stuck on top of each other or become slightly offset relative each other. This can make the final helix extension length unreliable and differ from one implantable medical lead to another implantable medical lead.

There is, thus, a need for improvements to implantable medical leads of the active fixation type.

SUMMARY

It is a general objective to provide an improved implantable medical lead. It is a particular objective to provide an implantable medical lead of the active fixation type that can functionally operate without any contact spring. These and other objectives are met by embodiments as disclosed herein.

An aspect of the embodiments relates to an implantable medical lead comprising a proximal lead portion, a distal lead portion and a lead body interconnecting the proximal and distal lead portions. The lead body has a lumen with a conductor coil running in the lumen. The proximal lead portion comprises a connector pin that is connected to a first end of the conductor coil. The distal lead portion has a tubular header with a lumen in which a fixation helix is at least partly provided. The fixation helix is mechanically connected to a first end of a shaft having its second end mechanically and electrically connected to the second end of the conductor coil. A tubular coupling is mechanically connected to the tubular header and is coaxially arranged relative the shaft with the shaft running in its lumen. Rotation of the conductor coil, the shaft and the fixation helix is transformed by a rotation-totranslation transforming element into a longitudinal movement of the fixation helix relative the tubular header and the tubular coupling.

The implantable medical lead also comprises a friction device in the form of a circumferential or circumferentially distributed element of an elastically deformable, flexible polymer-based material. The circumferential or circumferentially distributed element is arranged between the shaft and the tubular coupling or between the shaft and the tubular header. Regardless of arrangement site in the distal lead portion, the friction device is configured to oppose rotation of the shaft relative the tubular header and the tubular coupling.

The friction device thereby prevents unintentionally movement of the fixation helix out of the most distal end of the implantable medical lead, for instance during shipping and handling of the implantable medical lead. Furthermore, the friction device prevents the fixation helix to move out of the distal lead portion during implantation of the implantable medical lead when the lead is introduced into and moved inside a subject's body. However, by applying a sufficient torque on the connector pin in the proximal lead portion the friction forces caused by the friction device are overcome causing a rotation of the conductor coil, the shaft and the fixation helix and thereby an extension or the fixation helix out of the distal lead portion or a retraction of an extended fixation helix back into the distal lead portion.

A friction device of an elastically deformable, flexible polymer-based material configured to oppose rotation of the shaft and the fixation helix relative the tubular header and the tubular coupling provides several advantageous over a contact spring according to the prior art. The friction device will not cause any unpredictable increased friction between the post and the fixation helix, which is generally experienced as a non-repeatable helix performance. There is no risk of jumpiness during extension and retraction of the fixation helix or risk of a jammed but not fully extended fixation helix with the friction device. Variations in the compression of the contact spring as discussed in the background section are also circumvented by the embodiments as is any risk of compressed turns of the contact spring becoming stuck on top of each other or becoming slightly offset relative each other.

BRIEF DESCRIPTION OF THE DRAWINGS

The invention, together with further objects and advantages thereof, may best be understood by making reference to the following description taken together with the accompanying drawings, in which.

DETAILED DESCRIPTION

Throughout the drawings, the same reference numbers are used for similar or corresponding elements. The embodiments generally relate to implantable medical leads and in particular to an implantable medical lead of the so-called active fixation type having a fixation helix for anchoring the implantable medical lead into a target tissue in a subject, preferably a mammalian subject and more preferably a human subject.

Figure 1:
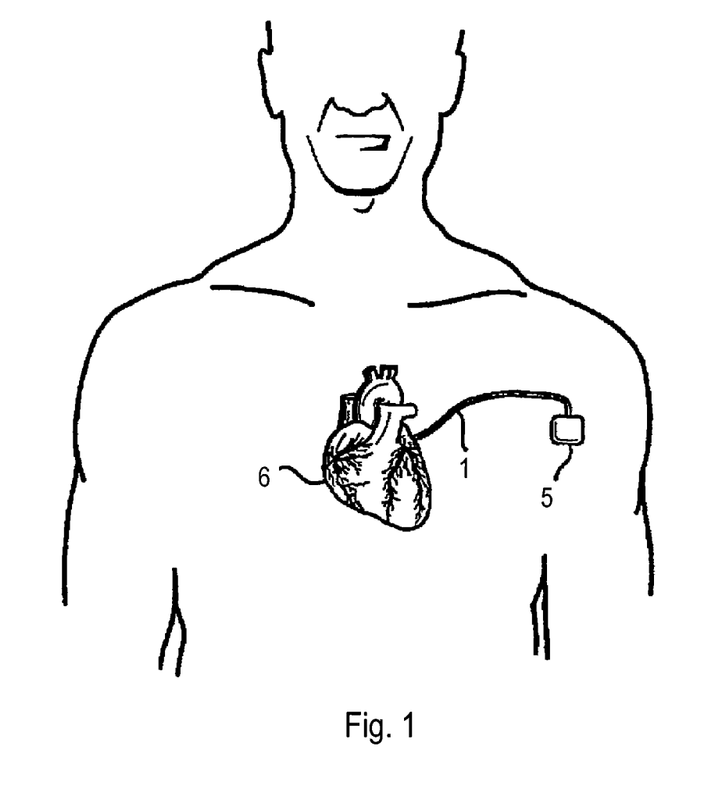
FIG. 1 is a schematic overview of a human subject having an implantable medical device connected to an implantable medical lead according to an embodiment.

FIG. 1 is a schematic overview of a human subject having an implantable medical lead 1 according to an embodiment. The implantable medical lead 1 is configured to be, during operation and use in the subject's body, connected to an implantable medical device (IMD) 5, such as a pacemaker, cardioverter or defibrillator. The implantable medical lead 1 then provides the electrical connection between the IMD 5 and the target tissue, represented by a heart 6 in FIG. 1. The implantable medical lead 1 is employed to apply therapy to the heart 6 in the form of pacing pulses and/or defibrillation shocks generated by the IMD 5. The implantable medical lead 1 can additionally or alternatively be used for sensing various physiological properties of the heart 6, such as electric signals induced in the heart 6.

The implantable medical lead 1 of the embodiments does not necessarily have to be employed for cardiogenic applications but can instead be used in connection with other target tissues. Non-limiting examples include spinal stimulation, neurostimulation, gastric stimulation, etc.

Figure 2:
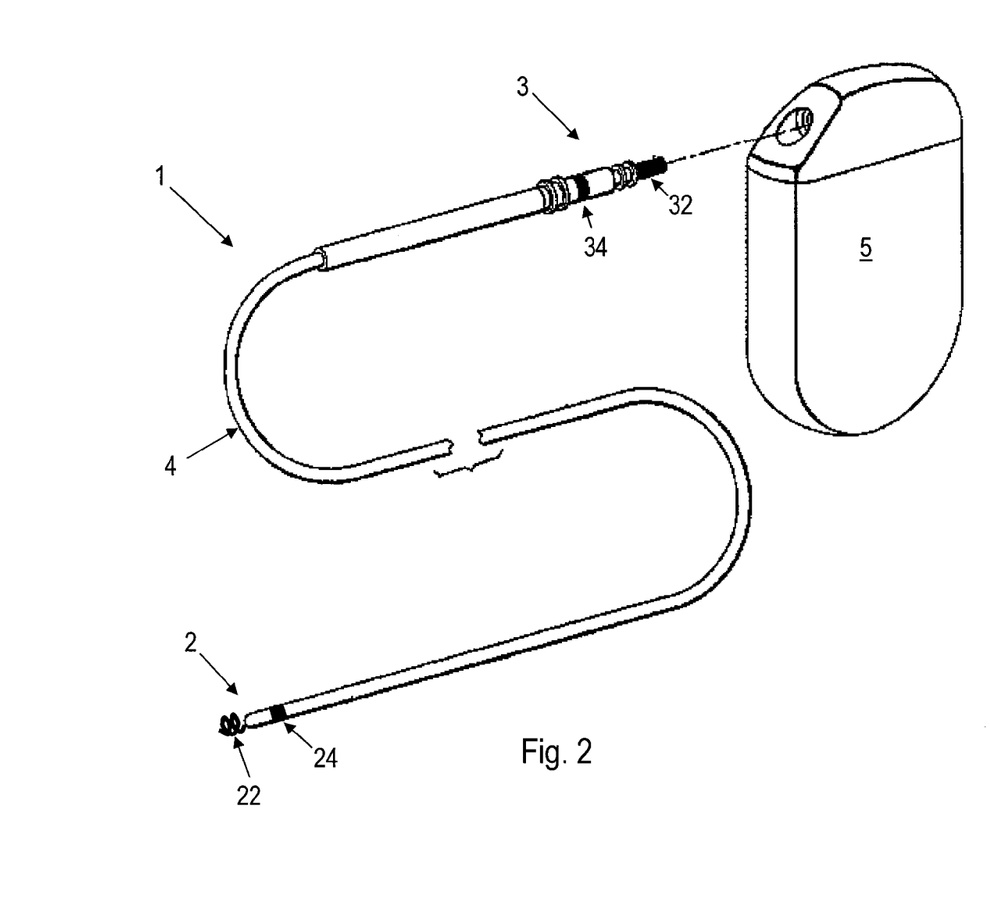
FIG. 2 is a schematic overview of an implantable medical lead according to an embodiment connectable to an implantable medical device.

FIG. 2 is a schematic overview of an implantable medical lead 1 according to an embodiment. The implantable medical lead 1 comprises a distal lead portion 2 designed to be introduced into a suitable pacing site to enable delivery of pacing pulses and sensing electric activity of the tissue, such as heart, at the particular pacing site. At least one electrode, two electrodes 22, 24 in FIG. 2, generally denoted pacing and sensing electrodes in the art, are arranged in connection with the distal lead portion 2. It is these electrodes 22, 24 that deliver pacing pulses to the tissue and capture electric signals originating from the tissue. The implantable medical lead 1 of FIG. 2 has been exemplified as a bipolar implantable medical lead 1 having one helical fixation electrode 22 and one ring electrode 24. This should merely be seen as an illustrative but non-limiting example and the embodiments also encompass other electrode configurations, such as unipolar and multipolar leads, including tripolar and quadropolar leads. The common feature of the implantable medical leads 1 of the embodiments is that they all comprise a fixation helix, which could constitute one of the electrodes or be electrically inactive.

An opposite or proximal lead portion 3 of the implantable medical lead 1 is configured to be mechanically and electrically connected to an IMD 5. The IMD 5 can be any implantable medical device used in the art for generating and applying, through the implantable medical lead 1, electric pulses or shocks to tissues. The IMD 5 is advantageously a pacemaker, defibrillator or cardioverter to thereby have the implantable medical lead 1 implanted in or in connection to a ventricle or atrium of the heart. However, also other types of IMDs 5 that are not designed for cardiac applications, such as neurological stimulator, gastric stimulator, physical signal recorders, etc. can be used as IMDs 5 to which the implantable medical lead 1 can be connected.

The proximal lead portion 3 comprises electrode terminals 32, 34 that provide the electric interface of the implantable medical lead 1 towards the IMD 5. Thus, each electrode terminal 32, 34 is arranged to be connected to a respective connector terminal in the IMD 5 to thereby provide electric connection between the IMD 5 and the electrodes 22, 24 through the electrode terminals 32, 34 and respective conductors running in a lead body 4.

The implantable medical lead 1 typically comprises a respective electrode terminal 32, 34 for each electrode 22, 24 in connection with the distal lead portion 2.

The implantable medical lead 1 also comprises the above-mentioned lead body 4 running from the proximal lead portion 3 to the distal lead portion 2. This lead body 4 comprises an insulating tubing having a lumen or bore. The lumen is designed and dimensioned to house at least one conductor coil that provides the electrical connection between the at least one electrode 22, 24 and the at least one electrode terminal 32, 34.

In a particular embodiment, one of the electrode terminals is in the form of a so-called connector pin 32 that is connectable to the IMD 5 and is rotatable relative the lead body 4. The connector pin 32 is mechanically and electrically connected to a first end of a conductor coil running in the lumen of the lead body 4. Rotation of the connector pin 32 is, through the mechanical connection to the conductor coil, transformed into a rotation and a longitudinal movement of the fixation helix 22, which is further described herein.

Figure 3:
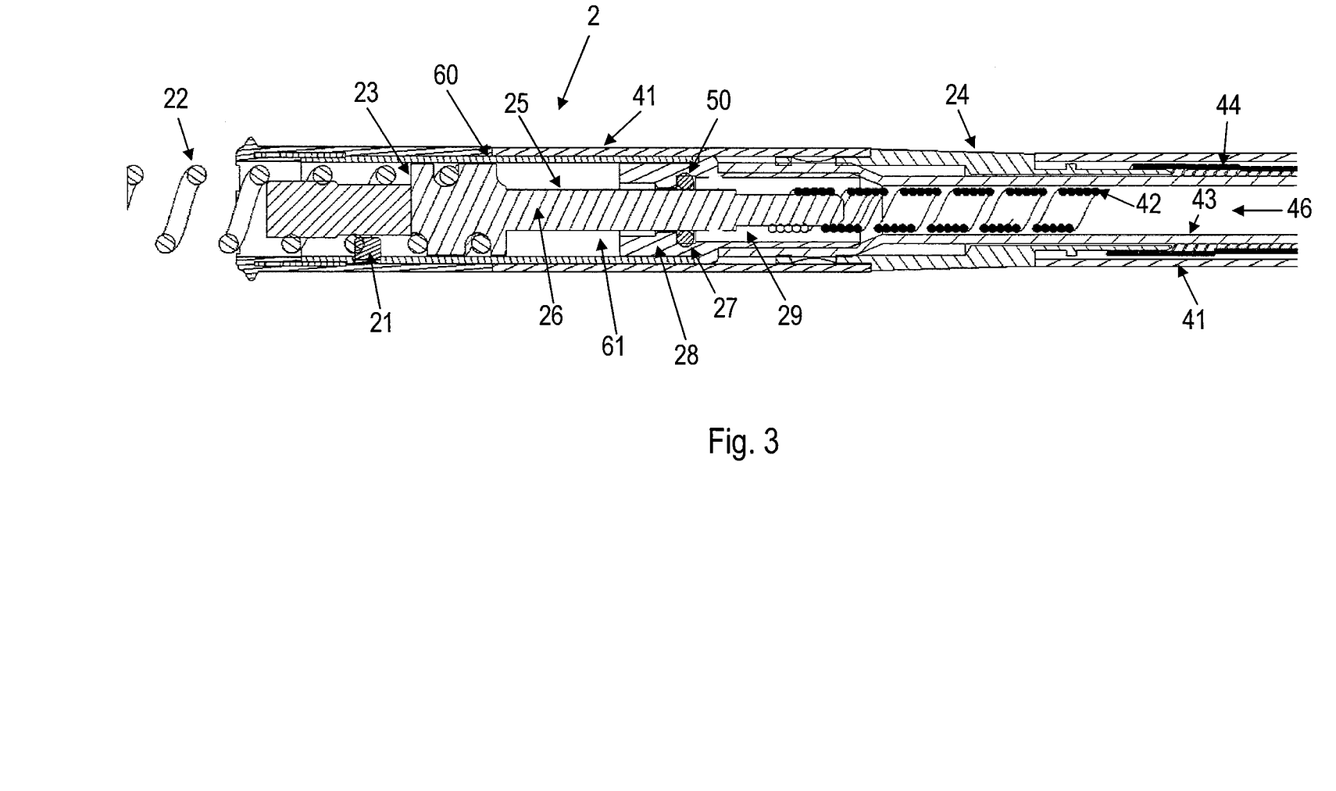
FIG. 3 is a cross-sectional view of a distal portion of an implantable medical lead according to an embodiment.

FIG. 3 is a cross-sectional view of the distal lead portion 2 and a part of the lead body according to an embodiment. The lead body comprises an outer insulating tubing 41 having a lumen 46 housing the conductor coil 42. In the illustrated embodiment, a second or outer conductor coil 44 is also running in the lumen 46 of the lead body and is electrically connected to a ring electrode 24. The inner conductor coil 42 and the outer conductor coil 44 are electrically insulated from each other in the lead body by an inner insulating tubing 43.

The distal lead portion 2 comprises a tubular header 60 having a lumen or bore 61. A fixation helix 22 is at least partly provided in the lumen 61 of the tubular header 60. The tubular header 60 can be of an electrically insulating material, such as a polymer or plastic material. Alternatively, the tubular header 60 is made of an electrically conducting material, which is further discussed herein.

The fixation helix 22 is mechanically connected to a first end of a shaft 26 provided in the lumen 61 of the tubular header 60. In an embodiment, the fixation helix 22 is welded to the shaft 26 and the attachment of the fixation helix 22 to the shaft 26 can be strengthened by providing grooves in connection with the first end of the shaft 26 in which an end of the fixation helix 22 is entered as shown in FIG. 3. Thus, the fixation helix 22 is advantageously fixedly attached to the shaft 26. The second, opposite end of the shaft 26 is mechanically and electrically connected to an end of the inner conductor coil 42. In some embodiments, the fixation helix 22 is an electrode, i.e. a helical fixation electrode 22. In such a case, there is both a fixed mechanical connection and an electrical connection between the helical fixation electrode 22 and the connector pin 32 illustrated in FIG. 2 through the inner conductor coil 42 and the shaft 26.

The distal lead portion 2 also comprises a tubular coupling 28 that is mechanically connected to the tubular header 60. The tubular coupling 28 is preferably fixedly attached to the tubular header 60. The tubular coupling 28 is coaxially arranged relative the shaft 26 and has a lumen or bore 29 in which a portion of the shaft 26 is running.

The assembly of the fixation helix 22, the shaft 26 and the inner conductor coil 42 is then rotatable relative the tubular header 60 and the tubular coupling 28. Rotation of the assembly as affected by rotating the connector pin in connection with the proximal lead portion is transformed into a longitudinal movement of the fixation helix 22 into or out of the distal end of the implantable medical lead. The transformation of the rotation into the longitudinal movement is achieved by a rotation-to-translation transforming element 21 arranged in the distal lead portion 2 and configured to engage the fixation helix 22 and transform a rotation of the fixation helix 22 into a longitudinal movement of the fixation helix 22 relative the tubular header 60.

Various types of such rotation-to-translation transforming elements 21 have been proposed within the technical field and can be used in the implantable medical lead. FIG. 3 illustrates one example of such a rotation-to-translation transforming element 21 in the form of a post 21 projecting inwardly into the lumen 61 of the tubular header 60. The post 21 is thereby provided between adjacent turns of the fixation helix 22 and transforms a helix rotation to a longitudinal helix movement. The embodiments are, though, not limited to such post-based implementations of the rotation-to-translation transforming element 21 but other known variants and alternatives can instead be employed.

Figure 4:
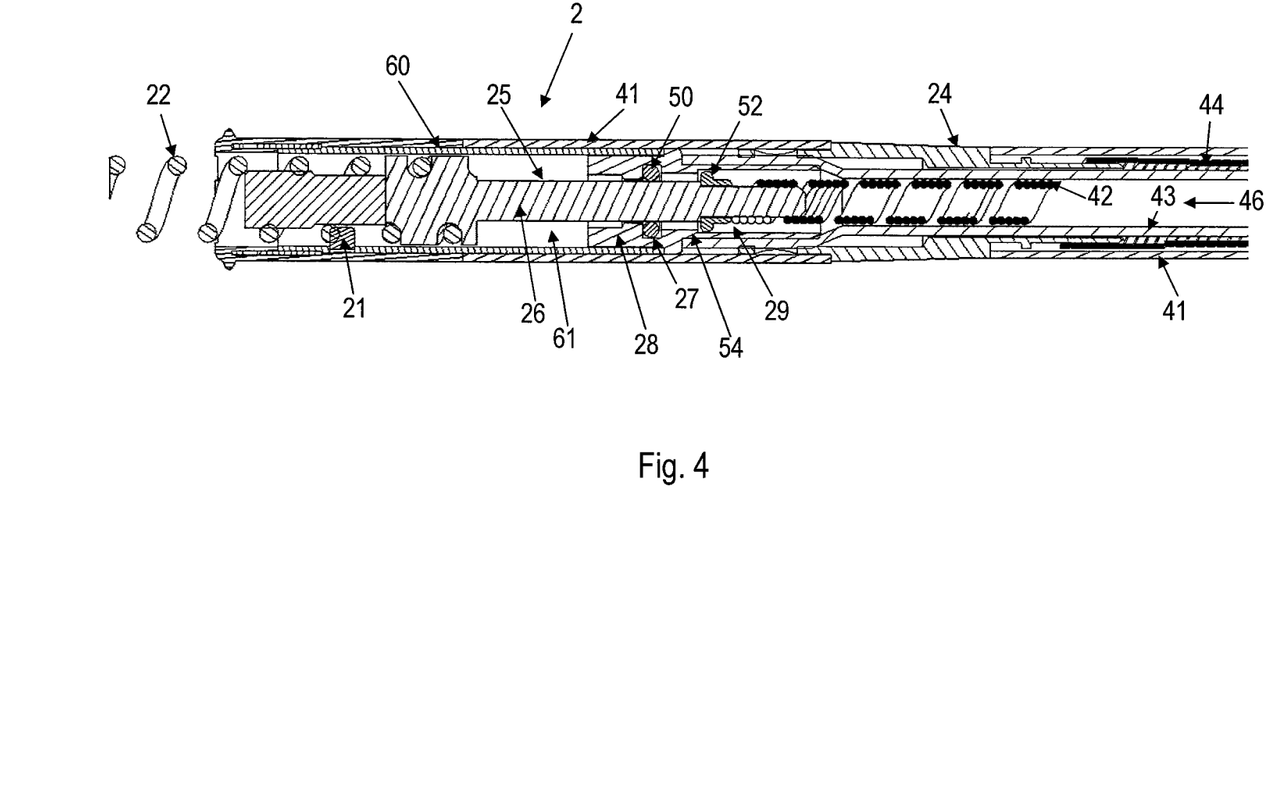
FIG. 4 is a cross-sectional view of a distal portion of an implantable medical lead according to another embodiment.

According to some embodiments as seen in FIGS. 3 and 4, a friction device 50 is provided in the distal lead portion 2 between the shaft 26 and the tubular coupling 28 or, is at least partly provided in an interface between the shaft 26 and the tubular coupling 28. Alternatively, as is further illustrated in FIG. 5, the friction device 50 is arranged between, such as at least partly provided in an interface between, the shaft 26 and the tubular header 60. The friction device 50 is in the form of a circumferential or circumferentially distributed element of an elastically deformable, flexible polymer-based material. The friction device 50 will thereby provide friction forces that oppose the rotation of the shaft 26 relative the tubular header 60 and the tubular coupling 28. This means that the friction device 50 prevents the fixation helix 22 from "spontaneously" and unintentionally moving out of the tubular header 60, for instance during transport or handling of the implantable medical lead and/or during implantation and passage of the implantable medical lead in the subject's body. In addition, the friction device 50 similarly prevents or restrains unintentional rotation and movement of the fixation helix 22 back into the distal lead portion 2.

Figure 5:
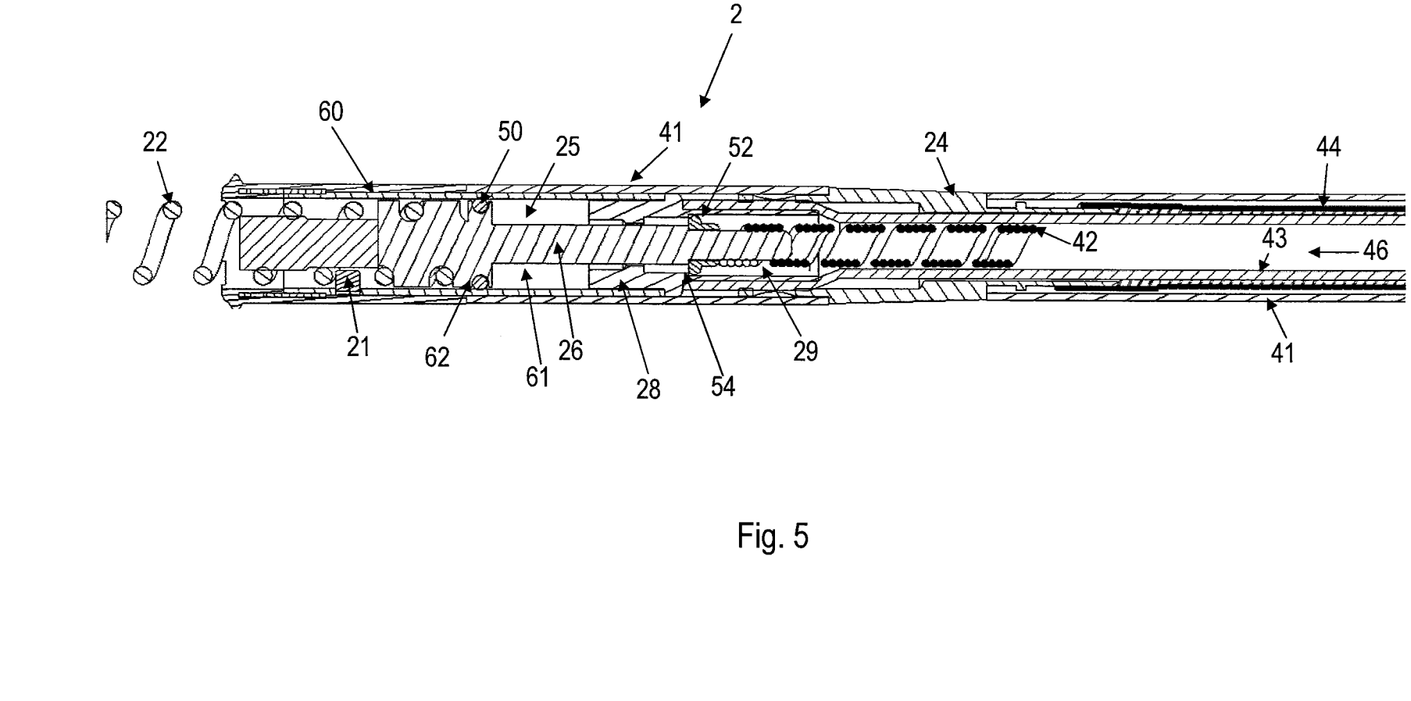
FIG. 5 is a cross-sectional view of a distal portion of an implantable medical lead according to a further embodiment.

However, the friction forces between the shaft 26 and the tubular coupling 28 or the tubular header 60 do not fully prevent rotation of the assembly of the fixation helix 22, the shaft 26 and the inner conductor coil 42 relative the tubular header 60 and the tubular coupling 28. Thus, by applying a sufficient torque at the connector pin in connection with the proximal lead portion the friction forces are overcome to thereby allow rotation of the assembly and longitudinal movement of the fixation helix 22 out of or back into the distal lead portion 2. The friction device 50 is thereby not a rotation lock but merely opposes but does not fully stop the rotation of the shaft 26 relative the tubular header 60 and the tubular coupling 28.

In a particular embodiment, the friction device 50 presents friction forces that are sufficient to restrain rotation of the shaft 26 and the fixation helix 22 relative the tubular header 60 and the tubular coupling 28 up to a defined minimum torque applied to the connector pin. However, if the applied torque exceeds the defined minimum torque the friction forces are overcome and the shaft 26 and the fixation helix 22 will start to rotate relative the tubular header 60 and the tubular coupling 28. The defined minimum torque required to rotate and translate the fixation helix 22 depends on particular material properties of the friction device 50, how tightly the friction device 50 engages and grips on the shaft 26, or the tubular header 60 or the tubular coupling 28 and the contact area between the friction device 50 and the shaft 26 or the tubular header 60 or the tubular coupling 28. These parameters can therefore be selected when designing the implantable medical lead. The defined minimum torque is typically selected to be in the interval of 0.01 to 0.1 Nmm, such as in the interval of 0.02 to 0.1 Nmm. The values of the defined minimum torque prevent unintentional movement of the fixation helix 22 out of or into the distal lead portion 2 but are still low enough to be easily overcome by applying a torque on the connector pin.

The friction device 50 is in an embodiment arranged between the shaft 26 and the tubular coupling 28, for instance as illustrated in FIG. 3. In such a case, the inner surface of the tubular coupling 28 has a circumferential groove 27 in which the friction device 50 is arranged. The friction device 50 is then advantageously in the form of a ring 51 (see FIGS. 6-8) that is entered in the circumferential groove 27 and extends slightly beyond the inner surface of the tubular coupling 28 to engage the outer or lateral surface 25 of the shaft 26 and thereby achieve the rotation opposing effect. An alternative approach (not shown) is to provide a groove in the outer surface 25 of the shaft 26 with the friction device 50 in the groove. The friction device 50 will then extend slightly beyond the outer surface 25 and engage the inner surface of the tubular coupling 28.

The length of the fixation helix 22 when fully extended out of the distal lead portion 2 can be defined by the interaction between the post 21 and a stop surface 23 of the shaft 26. This stop surface 23 is the end surface of the shaft 26 facing the post 21. When rotating the assembly of the fixation helix 22, the shaft 26 and the inner conductor coil 42, the fixation helix 22 is moved longitudinally out of the lumen 61 of the tubular header 60. At the same time the stop surface 23 approaches and eventually comes into contact with the post 21. The shaft 26 can then not be moved any further in this direction, i.e. towards the distal end of the implantable medical lead. This further prevents the fixation helix 22 from being moved further longitudinally in this direction relative the tubular header 60.

FIG. 4 is a cross-sectional view of another embodiment of the distal lead portion 2. In this embodiment, the outward, longitudinal movement of the fixation helix 22 is prevented by the interaction of a stop element 52 and a shoulder 54. The stop element 52 is arranged on the outer surface 25 of the shaft 26 and is configured to engage a shoulder 54 of the tubular coupling 28. When the stop element 52 comes into contact with the shoulder 54 the longitudinal movement of the shaft 26 and the fixation helix 22 in the direction out of the tubular header 60 is prevented.

FIG. 5 illustrates a cross-sectional view of a further embodiment of the distal lead portion 2. In clear contrast to the embodiments illustrated in FIGS. 3 and 4, the friction device 50 is in this embodiment arranged in a circumferential groove 62 in an outer surface 25 of the shaft 26. The friction device 50 thereby extends slightly beyond the outer surface 25 and engages the inner surface of the tubular header 60 to oppose rotation of the shaft 26 and the fixation helix 22 (and the inner conductor coil 42) relative the tubular header 60 and the tubular coupling 28. Thus, in this embodiment the friction device 50 is arranged between the shaft 26 and the tubular header 60. In an alternative variant (not shown), the circumferential groove is instead provided in the inner surface of the tubular header 60 with the friction device 50 in the groove. The friction device 50 will then engage the outer surface 25 of the shaft 26 to oppose the rotation of the shaft 26 and the fixation helix 22.

The arrangement of the friction device 50 between the shaft 26 and the tubular header 60 as illustrated in FIG. 5 can be combined with the embodiment of preventing further longitudinal movement as illustrated in FIG. 3, i.e. having a shaft 26 with a stop surface 23 configured to engage the post 21.

Figure 6:
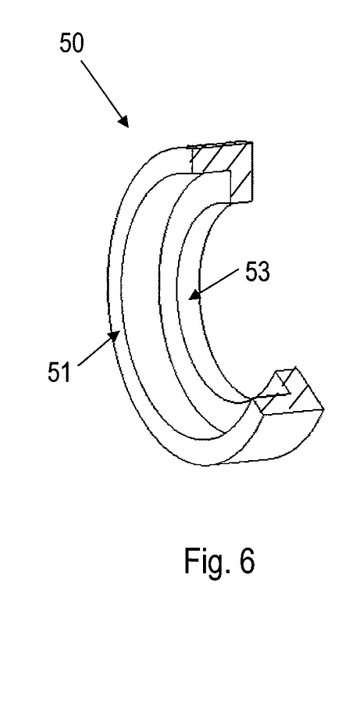
FIG. 6 illustrates an embodiment of a portion of a friction device.
Figure 7:
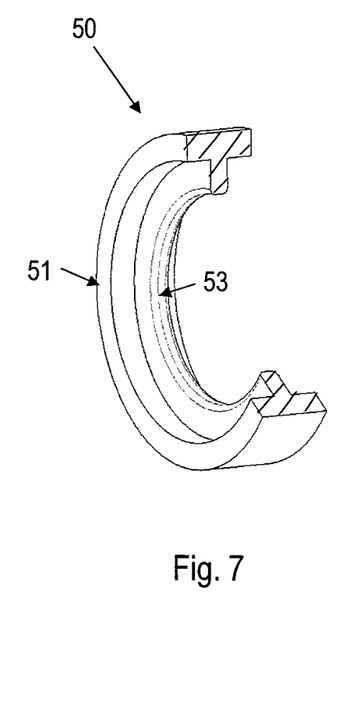
FIG. 7 illustrates another embodiment of a portion of a friction device.
Figure 8:
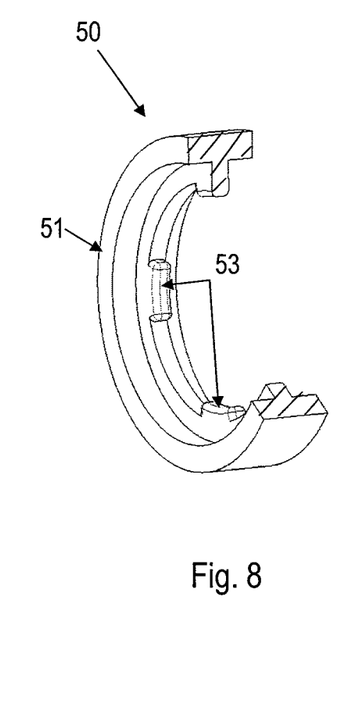
FIG. 8 illustrates a further embodiment of a portion of a friction device.

FIGS. 6 to 9 illustrate various embodiments of the friction device 50. In FIGS. 6 to 8 the friction device 50 is in the form of a ring 51 adapted to be arranged in a groove in the inner surface of the tubular coupling or the tubular header or in the outer surface of the shaft. The ring 51 could be a homogenous ring similar to an 0-ring. The ring thickness is then selected so that the inner or outer surface of the ring extends slightly beyond the inner surface of the tubular coupling/header or the outer surface of the shaft. Alternatively, the ring 51 could constitute a backbone of the friction device 50 with at least one protruding element 53 radially protruding from the ring 51 towards the center of the ring 51. In such a case, the ring 51 is arranged in the circumferential groove of the inner surface of the tubular coupling or the tubular header with the at least one protruding element 53 engaging the outer surface of the shaft to provide the friction forces opposing rotation of the shaft relative the tubular coupling or header. FIGS. 6 and 7 illustrate different friction devices 50 having a single protruding element 53 covering the whole inner circumference of the ring 51. In FIG. 6, the protruding element 53 is provided in connection with one of the sides of the ring 51 whereas in FIG. 7 the protruding element 53 is centrally arranged.

The friction device 50 of FIGS. 6 and 7 can have the effect of a blood seal in the distal lead portion. Thus, blood entering the distal lead portion from the opening through which the fixation helix can be extended will be prevented by the friction device 50 from reaching further inside the implantable medical lead beyond the position of the friction device 50 in the distal lead portion.

FIG. 8 illustrates the concept of having multiple circumferentially distributed protruding elements 53 radially protruding from the ring 51. Given the same type of material and the same thickness of the friction device in FIGS. 7 and 8, the applied friction forces will generally be larger with the friction device 50 of FIG. 7 as compared to the friction device 50 in FIG. 8 since the contact area between the friction device 50 and the shaft will the larger in FIG. 7 than in FIG. 8.

Figure 9:
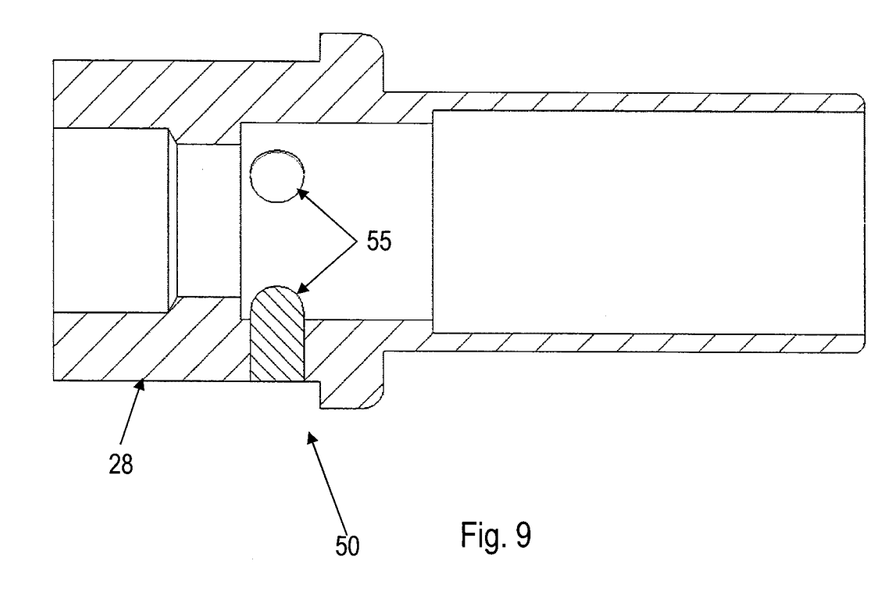
FIG. 9 illustrates a cross-sectional view of a tubular coupling with an embodiment of friction device.

The friction device embodiments of FIGS. 6 to 8 are all in the form of a circumferential element, i.e. having a continuous ring. The embodiments are, however, not limited thereto but can also use a friction device 50 in the form of a circumferentially distributed element as illustrated in FIG. 9. In this embodiment, the friction device 50 is in the form of multiple, i.e. at least two, separate protruding elements 55 that are directly arranged in the tubular coupling 28, the tubular header or in the shaft. In FIG. 9 only two such separate protruding elements 55 are shown but in other embodiments more than two separate protruding elements 55 could be employed, such as three, four or more. The separate protruding elements 55 are preferably evenly circumferentially distributed so that the angles between respective neighboring separate protruding elements 55 are the same, for instance 180° for two separate protruding elements 55, 120° for three separate protruding elements 55, 90° for four separate protruding elements 55 and so on.

If the separate protruding elements 55 are arranged in the tubular coupling 28 or in the tubular header, the tubular coupling 28 or the tubular header is preferably provided with through holes in which the separate protruding elements 55 are arranged as illustrated in FIG. 9. If the separate protruding elements 55 are instead arranged in the shaft, there are preferably a number of indentations in the outer surface of the shaft in which the separate protruding elements 55 are arranged.

The friction device is made of an elastically deformable, flexible polymer-based material. An example of such a polymer material is rubber. Other suitable examples include polyethylene, polyurethane and mixtures thereof, such as co-polymers of polyurethane and silicone.

The friction device can be molded in place, for instance in the groove of the tubular header or the tubular coupling or the shaft. Alternatively, the friction device can be pre-manufactured as one or multiple components and is then placed in the distal lead portion during assembly.

Usage of a friction device of an elastically deformable, flexible polymer-based material to oppose rotation of the shaft and the fixation helix relative the tubular header and the tubular coupling provides several advantageous over a contact spring according to the prior art as illustrated in FIGS. 10A and 10B. The friction device will not cause any unpredictable increased friction between the post and the fixation helix, which is generally experienced as a non-repeatable helix performance. There is no risk of jumpiness during extension and retraction of the fixation helix or risk of a jammed but not fully extended fixation helix with the friction device. Variations in the compression of the contact spring as discussed in the background section are also circumvented by the embodiments as is any risk of compressed turns of the contact spring becoming stuck on top of each other or becoming slightly offset relative each other.

In a particular embodiment, the tubular header and the tubular coupling are made of electrically conductive material, typically metal material. In such a case, there is a risk of chatter since the tubular header will have a free floating potential in relation to the shaft, the optional helical fixation electrode and the inner conductor coil. In the prior art, the contact spring is employed to prevent such chatter.

If the tubular header and typically the tubular coupling are made of electrically conductive material as the optional helical fixation electrode, the shaft and the inner conductor coil, the friction device is preferably a conductive friction device. The conductive friction device is then in the form of a circumferential or circumferentially distributed element of an elastically deformable, flexible polymer-based conductive material. The circumferential or circumferentially distributed element is arranged between the shaft and the tubular coupling or between the shaft and the tubular header. There the conductive friction device provides an electrical connection between the shaft and the tubular coupling or between the shaft and the tubular header in addition to opposing rotation of the shaft relative the tubular header and the tubular coupling.

In this embodiment, the friction device will, thus, have dual functions in terms of providing an electrical chatter-eliminating contact between the shaft and the tubular header/coupling and opposing unintentional rotation and longitudinal movement of the fixation helix.

The friction device is preferably made conductive by doping the polymer material with a conductive material. Any electrically conductive material that is compatible with the polymer material and can be doped therein can be used according to the embodiments as long as the conductive material is biocompatible and not toxic to the subject. Non-limiting examples of conductive materials that can be used include platinum, iridium, carbon and gold. The conductive material can be provided in any form that can be doped into the polymer material including, for instance, powder or flakes. Actually any conductive material that is traditionally employed in connection with implantable medical devices and that can be provided in a form to be doped with the polymer material is encompassed by and can be employed by the embodiments.

The fixation helix of the implantable medical lead can be made of a non-conductive material, such as a plastic or polymer material that has sufficient strength and rigidity to be screwed into a target tissue to anchor the implantable medical lead in the tissue. Alternatively, the fixation helix can be made of an electrically conducting material but is still electrically inert by having an outer electrical insulation, for instance by an electrically insulating layer or coating. In these embodiments, the fixation helix is not employed as an electrode for the implantable medical lead. In such a case, the most distal part of the implantable medical lead, connected to the tubular header, can be employed as electrode. The electrical connection between the most distal part and the inner conductor coil is provided by the shaft, the friction device and the tubular header or by the shaft, the friction device, the tubular coupling and the tubular header, depending on the actual position on the friction device in distal lead portion. The friction device is then made of a polymer-based conductive material to provide an electrical bridge or connection between the shaft and the tubular header or between the shaft and the tubular coupling.

In an alternative approach, the fixation helix is employed as an electrode, i.e. as a helical fixation electrode. In such a case, the whole fixation helix can be made of a conductive material. This conductive material can optionally be at least partly coated with an outer insulation. Part of the fixation helix will then be electrically active whereas remaining parts of the fixation helix will have an insulating surface layer. The electrical connection between the fixation helix and the inner conductor coil is, as has previously been discussed, achieved by the electrically conductive shaft.

The embodiments also encompass using multiple friction devices in the distal lead portion to provide the opposing forces. In such a case, at least one friction device is arranged between the shaft and the tubular header and/or at least one friction device is arranged between the shaft the tubular coupling. However, in most practical applications it is sufficient to use a single friction device.

The embodiments described above are to be understood as a few illustrative examples of the present invention. It will be understood by those skilled in the art that various modifications, combinations and changes may be made to the embodiments without departing from the scope of the present invention. In particular, different part solutions in the different embodiments can be combined in other configurations, where technically possible. The scope of the present invention is, however, defined by the appended claims.

What is claimed is:

1. An implantable medical lead comprising:
   a lead body having a lumen with a conductor coil running in the lumen;
   a proximal lead portion comprising a connector pin that is connected to a first end of the conductor coil and is connectable to an implantable medical device; and
   a distal lead portion comprising:
      a tubular header having a lumen;
      a fixation helix at least partly provided in the lumen of the tubular header, the fixation helix mechanically connected to a first end of a shaft having a second end mechanically and electrically connected to a second end of the conductor coil;

a tubular coupling mechanically connected to the tubular header, the tubular coupling coaxially arranged relative the shaft and having a lumen in which a portion of the shaft is running;

a rotation-to-translation transforming element configured to engage the fixation helix and transform a rotation of the fixation helix into a longitudinal movement of the fixation helix relative the tubular header and the tubular coupling; and a friction device in the form of a circumferential or circumferentially distributed element of an elastically deformable, flexible polymer-based material, the circumferential or circumferentially distributed element arranged between the shaft and the tubular coupling or between the shaft and the tubular header to oppose rotation of the shaft relative the tubular header and the tubular coupling.

2. The implantable medical lead of claim 1, wherein the friction device is in the form of a ring arranged in a circumferential groove in an inner surface of the tubular coupling, and the shaft runs through the ring.

3. The implantable medical lead of claim 2, wherein the ring comprises at least one protruding element radially protruding from the ring towards a center of the ring, the at least one protruding element configured to engage an outer surface of the shaft to provide friction forces opposing rotation of the shaft relative the tubular header and the tubular coupling.

4. The implantable medical lead of claim 1, wherein the friction device is attached to the tubular coupling and presents friction forces to an outer surface of the shaft to restrain rotation of the shaft relative the tubular header and the tubular coupling up to a defined minimum torque applied to the connector pin but allow rotation of the shaft relative the tubular header and the tubular coupling over the defined minimum torque applied to the connector pin.

5. The implantable medical lead of claim 1, wherein the friction device is attached to the tubular header and presents friction forces to an outer surface of the shaft to restrain rotation of the shaft relative the tubular header and the tubular coupling up to a defined minimum torque applied to the connector pin but allow rotation of the shaft relative said tubular header and said tubular coupling over the defined minimum torque applied to the connector pin.

6. The implantable medical lead of claim 1, wherein the friction device is attached to the shaft and presents friction forces to an inner surface of the tubular header to restrain rotation of the shaft relative the tubular header and the tubular coupling up to a defined minimum torque applied to the connector pin but allow rotation of the shaft relative the tubular header and the tubular coupling over the defined minimum torque applied to the connector pin.

7. The implantable medical lead of claim 1, wherein the friction device is attached to the shaft and presents friction forces to an inner surface of the tubular coupling to restrain rotation of the shaft relative the tubular header and the tubular coupling up to a defined minimum torque applied to the connector pin but allow rotation of the shaft relative the tubular header and the tubular coupling over the defined minimum torque applied to the connector pin.

8. The implantable medical lead of claim 1, wherein the friction device is in the form of a ring arranged in a circumferential groove in an outer surface of the shaft and is arranged to engage an inner surface of the tubular header.

9. The implantable medical lead of claim 1, wherein the friction device is in the form of a ring arranged in a circumferential groove in an outer surface of the shaft and is arranged to engage an inner surface of the tubular coupling.

10. The implantable medical lead of claim 1, wherein the friction device is in the form of a ring arranged in a circumferential groove in an inner surface of the tubular header and is arranged to engage an outer surface of the shaft.

11. The implantable medical lead of claim 1, wherein the rotation-to-translation transforming element is a post projecting inwardly into the lumen of the tubular header for transforming a rotation of the fixation helix into a longitudinal movement of the fixation helix relative the tubular header and the tubular coupling.

12. The implantable medical lead of claim 11, wherein the shaft comprises a stop surface configured to engage the post to prevent further longitudinal movement of the shaft and the fixation helix in a first direction relative the tubular header and the tubular coupling.

13. The implantable medical lead of claim 1, wherein the shaft comprises a stop element arranged on an outer surface of the shaft, the stop element configured to engage a shoulder of the tubular coupling to prevent further longitudinal movement of the shaft and the fixation helix in a first direction relative the tubular header and the tubular coupling.

14. The implantable medical lead of claim 1, wherein the friction device is a conductive friction device in the form of the circumferential or circumferentially distributed element of an elastically deformable, flexible polymer-based conductive material, the circumferential or circumferentially distributed element arranged between the shaft and the tubular coupling or between the shaft and the tubular header to provide an electrical connection between the shaft and the tubular coupling or between the shaft and the tubular header and oppose rotation of the shaft relative the tubular header and the tubular coupling.

15. The implantable medical lead of claim 14, wherein the polymer-based conductive material is a polymer material doped with conductive material.

16. The implantable medical lead of claim 15, wherein the polymer material is a rubber doped with a conductive material selected from the group of platinum, iridium, carbon and gold.

* * * * *